United States Patent
Khouri et al.

(10) Patent No.: US 9,744,275 B2
(45) Date of Patent: Aug. 29, 2017

(54) CONSTANT PRESSURE SYRINGE FOR SURGICAL USE

(75) Inventors: Roger K. Khouri, Key Biscayne, FL (US); Murat Kuru, Miami, FL (US)

(73) Assignee: Lipocosm LLC, Key Biscayne, FL (US)

( * ) Notice: Subject to any disclaimer, the term of this patent is extended or adjusted under 35 U.S.C. 154(b) by 797 days.

(21) Appl. No.: 12/633,477

(22) Filed: Dec. 8, 2009

(65) Prior Publication Data

US 2010/0137841 A1    Jun. 3, 2010

Related U.S. Application Data

(62) Division of application No. 11/768,902, filed on Jun. 26, 2007, now Pat. No. 8,968,272.

(Continued)

(51) Int. Cl.
*A61M 1/00* (2006.01)
*A61M 5/142* (2006.01)
(Continued)

(52) U.S. Cl.
CPC .......... *A61M 1/008* (2013.01); *A61M 1/0009* (2013.01); *A61M 1/0023* (2013.01);
(Continued)

(58) Field of Classification Search
CPC ................ A61M 1/0009; A61M 1/008; A61M 5/14216; A61M 5/1452; A61M 39/24;
(Continued)

(56) References Cited

U.S. PATENT DOCUMENTS 3,361,161 A    1/1968  Schwartz
3,572,375 A    3/1971  Rosenberg
(Continued)

OTHER PUBLICATIONS

Office Action for U.S. Appl. No. 11/768,902 dated Jul. 8, 2010.
(Continued)

*Primary Examiner* — Tatyana Zalukaeva
*Assistant Examiner* — Benjamin Klein
(74) *Attorney, Agent, or Firm* — Finnegan, Henderson, Farabow, Garrett & Dunner, LLP

(57) ABSTRACT

A closed system for harvesting fat through liposuction, concentrating the aspirate so obtained, and then re-injecting the concentrated fat into a patient comprises as its main components a low pressure cannula having between about 7 to 12 side holes of about 1-2 mm by 2.0 to 4.0 mm, a spring loaded syringe holder with a constant force or coiled ribbon spring to apply a substantially constant pressure over the full excursion of the plunger, and a preferably flexible collection bag which is also preferably graduated, cylindrical over most of its body and funnel shaped at its bottom, all of which are connected through flexible tubings to a multi-port valve. The multi-port valve has two flutter/duck bill valves which restrict the fluid flow to a one way direction which effectively allows the syringe to be used to pump fat out of a patient and into a collection bag in a continuous manner. After the bags are centrifuged to concentrate the fat, the excess fluids are separated and the valve is re-connected to permit the syringe pump to reverse fluid flow to graft the concentrated fat back into the patient.

23 Claims, 8 Drawing Sheets

Related U.S. Application Data

(60) Provisional application No. 60/828,505, filed on Oct. 6, 2006.

(51) Int. Cl.
*A61M 5/145* (2006.01)
*A61M 39/24* (2006.01)

(52) U.S. Cl.
CPC ....... *A61M 5/1452* (2013.01); *A61M 5/14216* (2013.01); *A61M 39/24* (2013.01); *A61M 2202/0021* (2013.01); *A61M 2202/08* (2013.01); *A61M 2205/073* (2013.01); *Y10T 137/7838* (2015.04); *Y10T 137/87249* (2015.04)

(58) Field of Classification Search
CPC .......... A61M 2202/08; Y10T 137/7838; Y10T 137/87249
USPC .......................................... 604/119, 311, 542
See application file for complete search history.

(56) References Cited

U.S. PATENT DOCUMENTS

| | | | |
|---|---|---|---|
| 3,788,047 A | | 1/1974 | Douthitt |
| 4,004,575 A | * | 1/1977 | Sarstedt .................... 600/578 |
| 4,051,852 A | | 10/1977 | Villari |
| 4,202,333 A | * | 5/1980 | Thill et al. .................... 604/135 |
| 4,381,006 A | * | 4/1983 | Genese .................... 604/135 |
| 4,404,924 A | * | 9/1983 | Goldberg et al. ............. 116/270 |
| 4,407,660 A | | 10/1983 | Nevens et al. |
| 4,430,079 A | * | 2/1984 | Thill et al. .................... 604/154 |
| 4,566,480 A | | 1/1986 | Parham |
| 4,775,365 A | | 10/1988 | Swartz |
| 4,863,429 A | * | 9/1989 | Baldwin .................... 604/135 |
| 4,993,452 A | | 2/1991 | Hough |
| 5,098,405 A | | 3/1992 | Peterson et al. |
| 5,380,287 A | * | 1/1995 | Kikuchi et al. ............... 604/135 |
| 5,722,956 A | * | 3/1998 | Sims et al. .................... 604/131 |
| 5,807,340 A | * | 9/1998 | Pokras .................... 604/183 |
| 5,814,023 A | * | 9/1998 | Fulk et al. .................... 604/232 |
| 6,463,318 B2 | * | 10/2002 | Prince .................... 600/420 |
| 6,585,005 B1 | | 7/2003 | Raftis et al. |
| 7,220,244 B2 | * | 5/2007 | Kriesel .................... 604/134 |
| 7,708,163 B2 | * | 5/2010 | Argentine .................... 222/1 |
| 8,412,310 B2 | * | 4/2013 | Liu et al. .................... 600/432 |
| 2001/0056259 A1 | | 12/2001 | Skinkle et al. |
| 2004/0039344 A1 | * | 2/2004 | Baldwin et al. .............. 604/209 |
| 2005/0048034 A1 | | 3/2005 | Fraser et al. |
| 2005/0215958 A1 | * | 9/2005 | Hawthorne .................. 604/227 |
| 2006/0093527 A1 | | 5/2006 | Buss |
| 2006/0100606 A1 | | 5/2006 | Dobak |
| 2006/0129092 A1 | | 6/2006 | Hanlon et al. |
| 2007/0251531 A1 | | 11/2007 | Khouri |
| 2010/0160900 A1 | | 6/2010 | Khouri et al. |

OTHER PUBLICATIONS

Office Action for U.S. Appl. No. 11/768,902 dated Feb. 25, 2010.
Gonzalez et al., "An Alternative Method for Harvest and Processing Fat Grafts: An In Vitro Study of Cell Viability and Survival", Plastic and Reconstructive Surgery Journal, 2007, pp. 285-294, vol. 120, No. 1.
Nguyen et al., "Comparative Study of Survival of Autologous Adipose Tissue Taken and Transplanted by Different Techniques", Plastic and Reconstructive Surgery Journal, 1990, pp. 378-396, vol. 85, No. 3.
Niechajev et al., "Long-term Results of Fat Transplantation: Clinical and Histologic Studies", Plastic and Resconstructive Surgery Journal, 1994, pp. 496-506, vol. 94, No. 3.
Office Action for U.S. Appl. No. 12/633,442 dated Mar. 22, 2012.
Rennekampff et al., "Current Perspective and Limitations of Autologous Fat Transplantation- "Consensus Meeting" of the German Society of Plastic, Reconstructive and Aesthetic Surgeons at Hannover; Sep. 2009", Handchir Mikrochir Plast Chir, 2010, vol. 42, Issue 2.
Office Action for U.S. Appl. No. 12/633,442 dated Sep. 7, 2012.
International Preliminary Report on Patentability (Chapter II) for PCT/US2008/068418 issued Sep. 17, 2009.

* cited by examiner

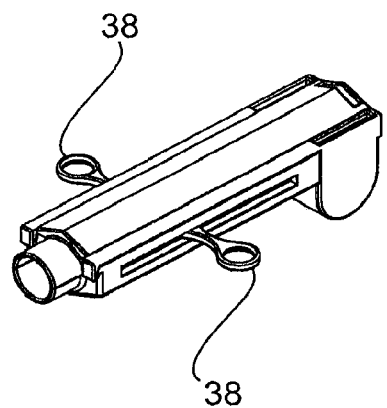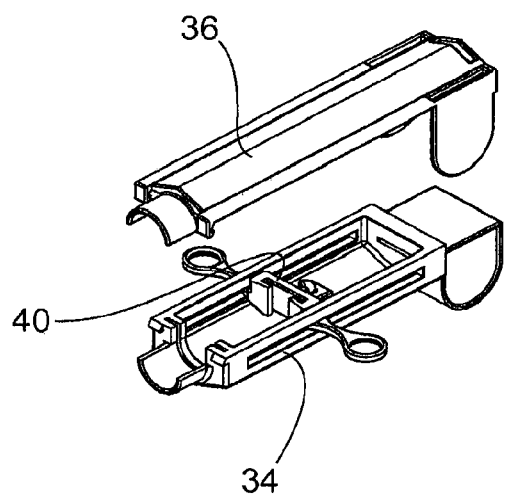
Fig. 2a
Fig. 2b
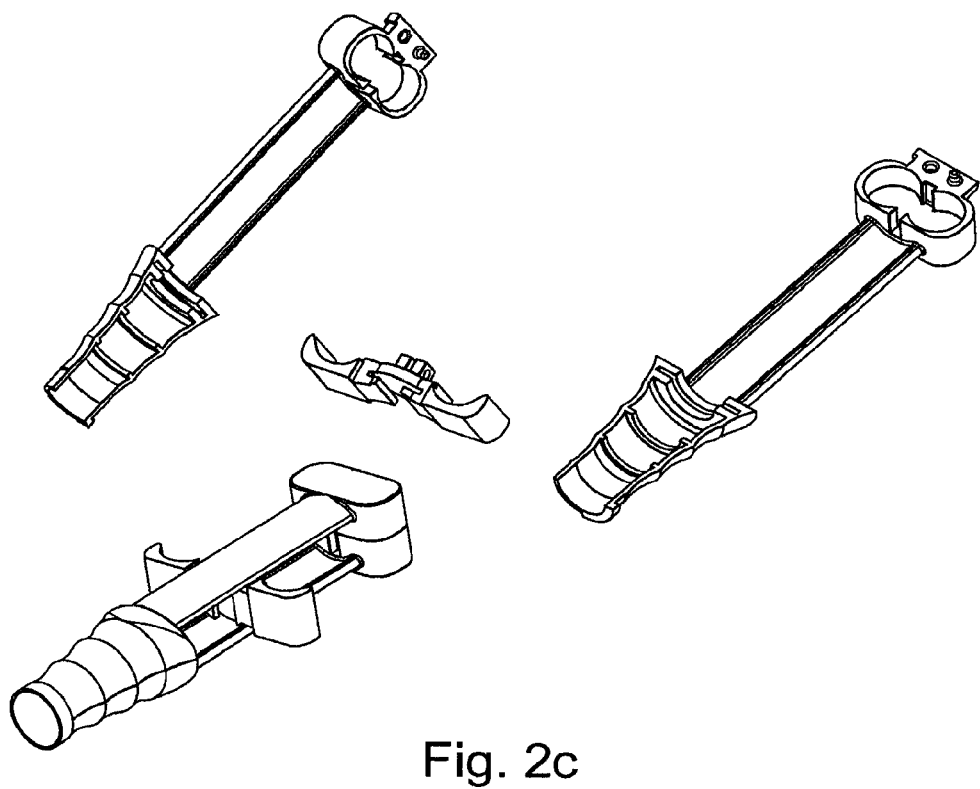
Fig. 2c

CONSTANT PRESSURE SYRINGE FOR SURGICAL USE

CROSS REFERENCE TO RELATED APPLICATION

Priority is claimed to provisional U.S. Patent Application Ser. No. 60/828,505 filed Oct. 6, 2006 entitled Method and Apparatus for Lipotransfer, the disclosure of which is incorporated herein by reference.

BACKGROUND AND SUMMARY OF THE INVENTION

The autologous grafting of liposuctioned tissue holds much promise in plastic surgery; but being very technique dependent, and lacking a simple apparatus to perform it, it has a reputation for being impractical and unreliable. Generally, as presently performed in the prior art, the process requires harvesting with suction cannulas delicate and finicky adipocytes, separating them, concentrating them, and then re-grafting them a droplet at a time into a three-dimensional recipient matrix in aliquots small enough to survive through diffusion yet separated enough to avoid crowding. The process becomes extremely arduous and time consuming when large volumes are involved. One of the inventors herein has previously invented methods and apparatus for performing fat grafting as shown in pending U.S. patent application Ser. No. 11/409,294, filed Apr. 21, 2006 and entitled Method and System for Preparing Soft Tissue for Grafting, Enhancing Grafting Results, and Grafting Autologous Fat to Soft Tissue Such as the Breast, the disclosure of which is incorporated herein by reference. This process and method represents a significant breakthrough and improvement over the prior are but leaves room for further improvement and refinement. The inventors herein have invented a system comprised of a number of devices each of which is novel but which also function together in a novel way to streamline, simplify and implement fat grafting with a practical procedure having a more predictable success.

The process of liposuction, or the harvest of subcutaneous fat, is commonly performed with a lipoaspirator machine that generates about one atmosphere vacuum pressure and has a collection flask connected in series between the suction cannula and the vacuum pump. It is well accepted that one atmosphere vacuum pressure is most effective if the intent is to simply remove and discard the fat to reduce excesses in body contour. However, if the intent is to reinject this aspirated tissue as a graft, one atmosphere pressure is too high as it inflicts significant damage to the adipocytes sufficient to render them undesirable for reinjection. Therefore, for the purpose of re-grafting or reinjection it is generally known that lower vacuum pressures, closer to one half an atmosphere should be used to yield better fat graft survival. If lower pressures are used however, it reduces the efficiency of liposuction.

The grafting of lipoaspirated fat is increasingly being recognized as a method of restoring volume defects and of improving body contour abnormalities such as may be found in the cheeks, the breast or the buttocks. In addition, tissue carefully harvested by liposuction has been shown to be rich in stem cells capable of regenerating tissue and of improving a number of conditions related to scarring, radiation damage and even aging. Therefore a method and device that would make this process of low pressure harvesting, processing and re-injecting lipoaspirated fat simple, practical and reliable would be of great utility.

The inventors have succeeded in developing such a system that utilizes a number of novel components uniquely suited to low pressure harvesting of lipoaspirated fat. Each of these components themselves have novel and inventive aspects to them, and together comprise a closed system that is uniquely suited to harvesting fat for reinjection.

The inventors closed system includes as its components a very low pressure, multiple opening, cannula for aspirating the fat from the patient; a constant, controlled low pressure syringe mechanism for controllably liposuctioning the aspirate out of the patient with minimal damage to the adipocytes; and a collection bag into which the aspirate is deposited. A multi-port routing valve interconnects these three components with several ports of the routing valve having internal duck bill valves for one way routing of the aspirate both as it is collected and as it is re-injected. Although reference is made throughout this disclosure to a duck bill or flutter valve, it should be understood that those terms apply to any design that opens completely and widely, with minimal pressure gradient, which avoids the slit-like openings of other valve constructions, for example, that force the fat cell suspension to be damaged as it accelerates through the narrow opening. To perform either of the aspiration or re-injection, the syringe mechanism is repeatedly operated to in effect "pump" the fluid through the multi-port routing valve with its one way internal valves. In this way, the aspirate is collected without being exposed to the atmosphere and at low pressures so as to minimize the damage to the delicate and sensitive adipocytes. After collection, the bag is disconnected from the routing valve and one or more bags may be centrifuged at low pressures, such as with a manual centrifuge, to separate the aspirate within each bag into its components of serum, concentrated fat and free oil. After being centrifuged, the supernatant oil is purged from the top of the bag, the serum fluid is purged from the bottom port, and the concentrated fat remains in the bag for re-injection. To perform re-injection, the bag and cannula are connected to the routing valve at each other's ports as used for aspiration. This connection one-way routes the concentrated fat out of bag into the patient by means of the duck bill valve orientation. Then, after the routing valve and cannula are primed, the very low pressure syringe is repeatedly operated to withdraw the concentrated fat from the bag, and then push it through the routing valve and into the patient. Alternatively, instead of the spring syringe system, a small 1-5 ml syringe is preferably used with a simple spring on the plunger which brings it automatically back each time the surgeon's fingers push down on it to empty the grafts into the patient. Throughout this process the aspirate is not exposed to the air, only very low pressures are used to move the aspirate through the system, a low speed centrifuge is used to concentrate the fat from the aspirate which can be collected into multiple bags to speed the concentration process, and the same system components used to collect the aspirate are used to re-inject the concentrated fat. This closed system and method provide significant improvements over the prior art, and will more fully understood by referring to the drawing figures and description of the preferred embodiment that follows.

BRIEF DESCRIPTION OF THE DRAWINGS

FIG. 2(a) is a perspective view of a spring activated syringe aspirator;

FIG. 2(b) is an exploded view of the aspirator of FIG. 2(a);

FIG. 2(c) is an exploded view of an alternate design aspirator with two smaller helicoidal springs;

DETAILED DESCRIPTION OF THE PREFERRED EMBODIMENT

Figure 1:
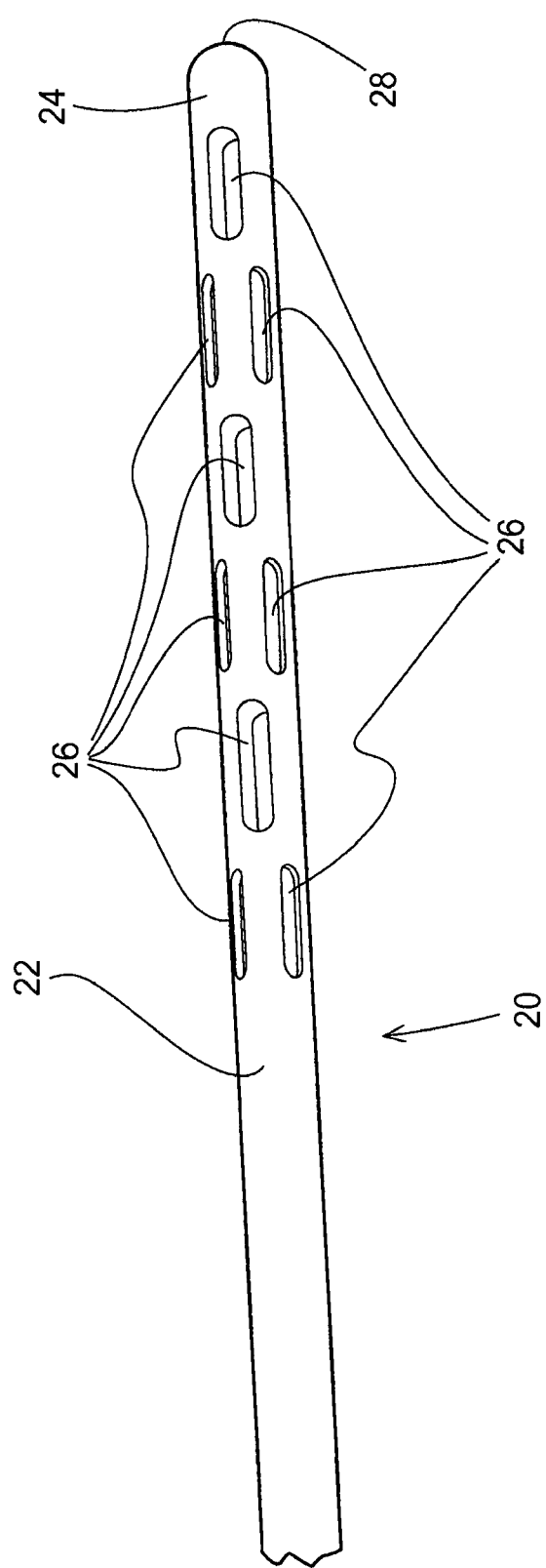
FIG. 1 is a side view of a multi-hole cannula suited for very low pressure harvesting of lipoaspirate.

As has become known in the art, grafted fat globules have to first survive by diffusion and what is called plasmatic imbibition until they get revascularized from the recipient bed. Larger globules that have a lower surface to volume ratio cannot get enough nutrients to survive and therefore die off before getting revascularized. This improved understanding of the physiology of graft survival led to the use of smaller bore cannulas with smaller openings that harvest smaller globules of fat. While generally speaking the smaller the better, very small is impractical in terms of harvesting efficiency, especially when large volumes are required for the particular procedure. It is well recognized today that the ideal harvesting cannulas should have diameters between 2-3 mm and harvesting slits (hole openings) between 0.5 and 3 mm.

The most commonly used and commercially available cannulas for liposuction are either blunt ended with a single side hole, three side holes (Mercedes type) or have an open end protected by a bucket handle-like shield (the Coleman harvesting cannula). While there are also some cannulas with up to six side holes, they are less popular, and to the inventors' knowledge, never scientifically proven to be superior to the more commonly used ones. Furthermore, with the standard pressures used for liposuction, it is commonly believed based on use that too many holes clog up the preferred small bore cannulas otherwise thought to be useful for this application.

The inventors are unaware of work in the prior art evidencing that progressively increasing the numbers of side holes, while maintaining the optimal catheter bore of 2.4-2.7 mm and the slit opening of about 1.0-2.0 mm by 2.0-4.0 mm can not only improve the efficiency of fat harvesting (volume harvested per to-and-fro stroke of the cannula) but also achieve excellent harvesting yield at vacuum pressures much lower than previously described.

In a study conducted by the inventors, a series of cannulas with increasing number of side holes (Coleman design, one, two, three and up to nine side holes) were connected to a liposuction aspirator machine that was progressively dialed down to the gentlest vacuum that would still yield a continuous flow of fat. In three patients the inventors measured at each pressure and with each cannula, the volume of lipoaspirate per 10 strokes in comparable fresh tumesced fields. The results confirmed that yield of fat per pass increased linearly with the number of side holes in the cannula. Cannulas with 9 holes proved most efficient at harvesting with pressures as low as 240 mm/Hg. Cannula diameter was best at 2.4 mm for the skinny patients and 2.7 mm for the more fibrous & obese. This, to the inventors' knowledge, establishes for the first time that liposuction can be effectively performed with excellent yield at very low pressures (250-350 mmHg or ⅓ atmospheric) that cause minimal damage to the tissue provided a cannula was used with 9-12 side slit like holes measuring about 1.0-2.0 mm by 2.0-4.0 mm depending upon the bore diameter. With increased bore size, larger holes it is thought could be effectively used to achieve similar results.

As shown in FIG. 1, a cannula 20 comprises a body 22 with a tip 24 which is inserted within a patient to harvest fat. The body has three series of holes 26, each series comprising three holes 26 aligned along the body length. The other side of the body 22 (not shown) is left intact. A central bore 28 may also be provided, as desired.

The inventors postulate that increasing the number of side holes beyond 9 and even up to 12 might further improve the process, and have found such results with 12 hole cannulas. However adding too many holes can become problematic for two reasons: (a)—structural: more side holes weaken the cannula and there is a real danger that the cannula could break while inside the patient requiring an incision and a scar to retrieve it (a complication that occurred when a poorly designed 12 side hole cannula was tried; and which would be avoided by the inventors arrangement of side holes not spread over the entire cross sectional circumference of the cannula but instead be limited to about half the circumference, leaving the other half circumference intact to maintain structural integrity); (b)—impractical: having too many side holes along the shaft of the cannula restricts the excursion range of the liposuction motion as the more proximal side holes cause loss of vacuum when the cannula is retracted close to the skin insertion site during the back and forth excursions required for liposuction.

The cannula length depends upon the requirements of the patient and the anatomical area to be harvested and the preference of the surgeon. We made cannulas for various uses that vary between 15 to 45 cm in length. To avoid breaks and maintain structural integrity the side holes are preferably aligned along half the circumference, keeping the remaining half structurally intact.

Liposuction with the intent to re-inject the harvested tissue is commonly performed using a syringe and manual pressure generation. The problem with this approach is not only cramping and fatigue of the operator's hand but also inability to effectively control the level of vacuum achieved. (The hand can generate very high vacuum pressures that will destroy a lot of the fat cells, and especially after fatigue and lack of control, the hand often pulls ineffectively with suboptimal pressures). Thus the need for a mechanically activated device that, once activated, would pull on the syringe plunger with a constant force throughout virtually its entire stroke from completely collapsed inward to full extension.

Figure 3:
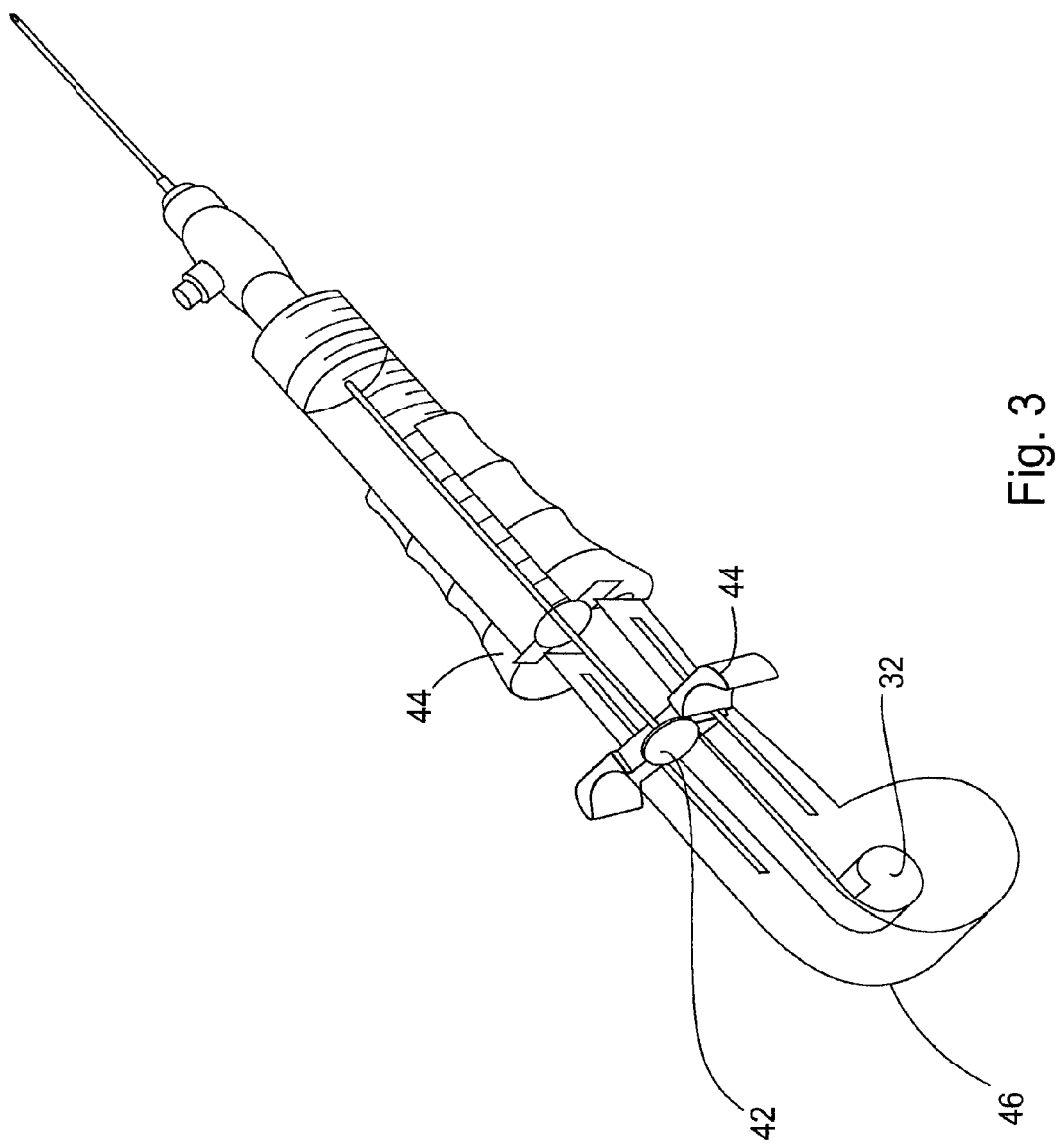
FIG. 3 is an assembled but transparent view of the syringe aspirator, with a syringe installed therein.

While the most simple mechanical design is a spring connected to the plunger, the problem is that commonly available coil springs do not have a flat stress strain curve, especially over the long range of excursion of the syringe plunger that are required for liposuction. We therefore invented an apparatus that pulls the plunger of a syringe over its entire excursion range with the same constant force to generate a constant controlled low atraumatic negative pressure of about 250-350 mmHg. This syringe holder 30 is shown in FIGS. 2 and 3. This apparatus includes either a set of springs judiciously designed and arranged to provide a constant force over the entire long range of excursion, or, preferably a specially designed spring construction that uncurls with a constant force, as shown as item 32 in FIG. 3.

The subject of the invention herein is preferably a device that can activate a syringe to pull a relatively constant controlled negative pressure over the entire range of its excursion. The inventors have conceived a number of designs whereby mechanical energy can be stored and then induced to deliver a constant pull force over substantially the entire range of excursion of the plunger. This includes hydraulic or gas pressure activated devices that are either self contained with the hydraulic energy stored within the device or devices that are connected to a source of hydraulic energy whether a gas tank or a separate pump. A gas tank of the kind generally available in the operating rooms connected to a pressure regulator device a hose and a mechanical transducer to activate the syringe plunger is also a alternative means of generating a constant vacuum pressure. Alternatively, a battery operated electric pump can also be the source of energy that can drive the syringe plunger with a constant force to generate a constant negative pressure over its entire range of excursion.

For a purely mechanical (no hydraulic and no electrical) design, there are a number of alternative means of connecting the syringe plunger to the spring, including direct connection or indirect with cables and pulleys. The device can be designed to accept standard disposable syringes and once cocked, can pull on syringe plunger to generate the desired constant vacuum. Alternatively, instead of the device being an activator for standard disposable syringes, the device can incorporate its own pistons and cylinders as a stand-alone device that does not need to be loaded with extraneous syringes.

As shown in greater detail in FIGS. 2 and 3, the syringe holder may be made from molded parts, such as a bottom receiver 34 and cover 36 (shown assembled in FIG. 2(a)). A pair of rings 38 extending from a bracket 40 provide a connection point for one or more springs (not shown). The custom made syringe device shown in FIG. 3 includes the syringe butt 42 encased in a handle 44. A spring casing 46 provides storage for the helicoidal spring 32, which is preferably used as has been found by the inventors to provide a relatively constant pressure over the course of its winding and unwinding.

Even if the vacuum pressure of the lipoaspirator machine is dialed down to atraumatic low levels, harvesting the fat with a vacuum source in series with the collection reservoir has been found by the inventors to be untenable for many reasons: 1—The collection bottle has to be rigid lest it collapses with the vacuum defeating its function as a reservoir; 2—The collection bottle has to remain vertical, lest the harvested fat continues its way with the aspirated air flow towards the vacuum pump. This is impractical as it forces the collection reservoir to remain on a dedicated stable fixed stand away from the mobile surgical field; 3—this requirement adds a few additional feet of tubing with significant opportunity for dead space losses to form; and most importantly, 4—adipocytes are well known to be damaged by dessication from high volume air flow and from air splashes in the collection bottle upon every instance of vacuum loss (and these tend to be quite frequent whenever one of the liposuction cannula holes gets close to the skin entrance site).

As an improvement over this prior art, the inventors have developed a fat harvesting apparatus whereby the vacuum source and the collection reservoir are not in series but are rather isolated from each other in a parallel type of configuration. To that effect, the inventors designed a routing valve that isolates the collection reservoir from the vacuum source and depending upon the applied pressure gradient directs the flow of fat aspirate either towards the vacuum source syringe or towards the collection bags used for separation and re-injection. Compared to manual liposuction whereby each time a syringe is filled, it has to be disconnected from the cannula and replaced with an empty one, not only is the requirement for syringe supplies reduced but more importantly the operating time has been found to be reduced by half.

While there are in the market a number of prior art valve based devices intended to direct the flow of an aspirate or an injectate from a reservoir to the recipient source or, acting in reverse from a source to a reservoir, these devices proved not suitable for this application where the fat is intended to be re-injected. The pressure gradient required to reverse flow from opening to closure of the valve is preferably as close to zero as possible. Hence, all the spring-based designs are not suitable. Furthermore, the flow across the valve has to be as unrestricted as possible to prevent the damaging high velocity/high shear flow that a slit like opening from the membrane based valve designs would necessarily impose. Similarly, the rotary valves and other ball valves tend to crush the adipocytes as they close.

The inventors have found that the duckbill and the flutter type of valves are preferred for this application, for the following reasons. They require very little pressure gradient to open, they open over the entire bore of the tubing, they close gently without snapping to cause minimal damage to the adipocytes, they have no added moving parts, and can be molded out of biocompatible rubber like material.

Figure 4:
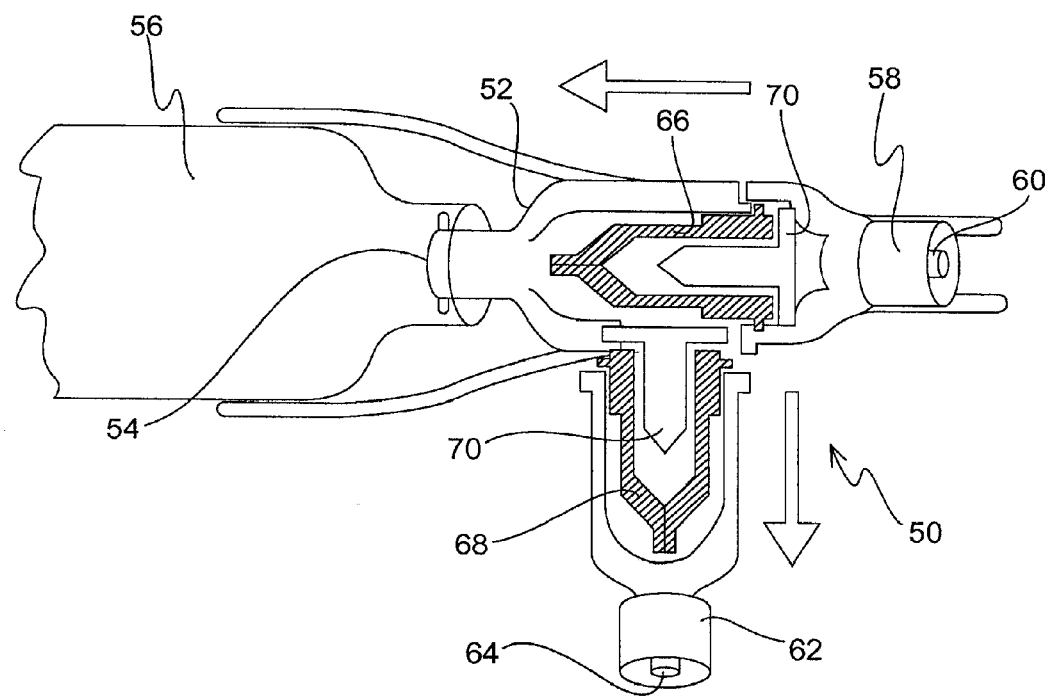
FIG. 4 is a side view of the routing valve, with cutaway detailing the various flow paths of aspirate therethrough.
Figure 5:
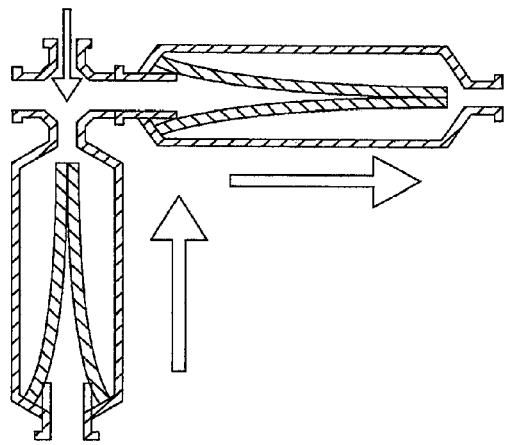
FIG. 5 is a schematic side view detailing the re-arrangement of the routing valve for re-injection of the fat into a patient.

Thus, the inventors developed a routing valve consisting of two duckbill or flutter valves positioned in the arrangement presented in FIG. 4 for harvesting and a reversed arrangement shown in FIG. 5 for re-injecting. However, a design modification described in FIG. 6 allows the same valve setup device to be used for both purposes provided a different fourth opening is plugged or connected to the syringe.

Figure 6:
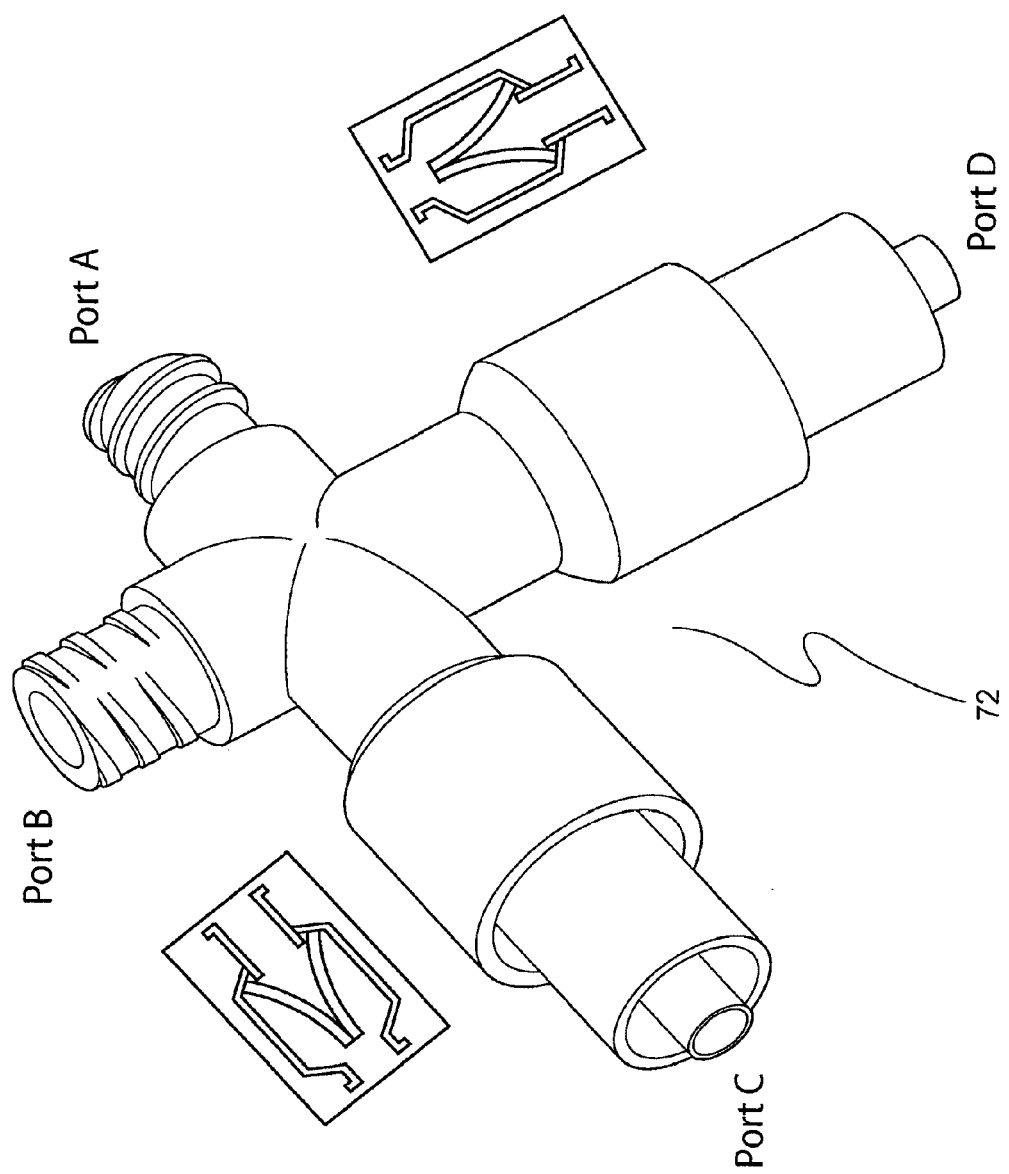
FIG. 6 is a side view of the routing valve detailing its arrangement of one way valves within it for multi-use such that the same routing valve may be used for both aspiration and re-injection, depending upon which of the open side ports is occluded and which is connected to the syringe.

More particularly, as shown in FIG. 4, a three port multi-valve 50 has a first port 52 for connection with, for example, a Luer lock 54 to a syringe 56, a second port 58 for connection with another Luer lock 60 to a cannula (not shown), and a third port 62 with a Luer lock (64) for connection to tubing (not shown) for carrying the aspirated fat to a collection bag (not shown). Each of ports 58 and 62 have an associated preferably rubber flutter/duck bill valve 66, 68 respectively which allow one way flow through their associated ports. Preferably, a hard inner sleeve 70 in each valve 66, 68 prevents eversion of the flutter/duck bill valve. As shown in FIG. 5, the valve 50 may be constructed with the flutter/duck bill valves oriented differently to allow for fat grafting or re-injection. As shown in FIG. 6, a four port multi-valve 72 may be provided to allow for either aspirating or grafting, merely be re-connecting the components to different ports. With the set up described above, free oil supernatant accumulation volume (a measure of adipocyte damage) and percentage graft take were at least as good as historical controls performed with a manual syringe. With the four port valve as shown in FIG. 6, in harvesting/aspiration mode, the cannula is connected to port D, the syringe to port B, the collection bag to port C and port A is plugged off. In injection/grafting mode, The cannula is connected to port C, the syringe to port A, the collection bag to port D and port B is plugged off.

Figure 7:
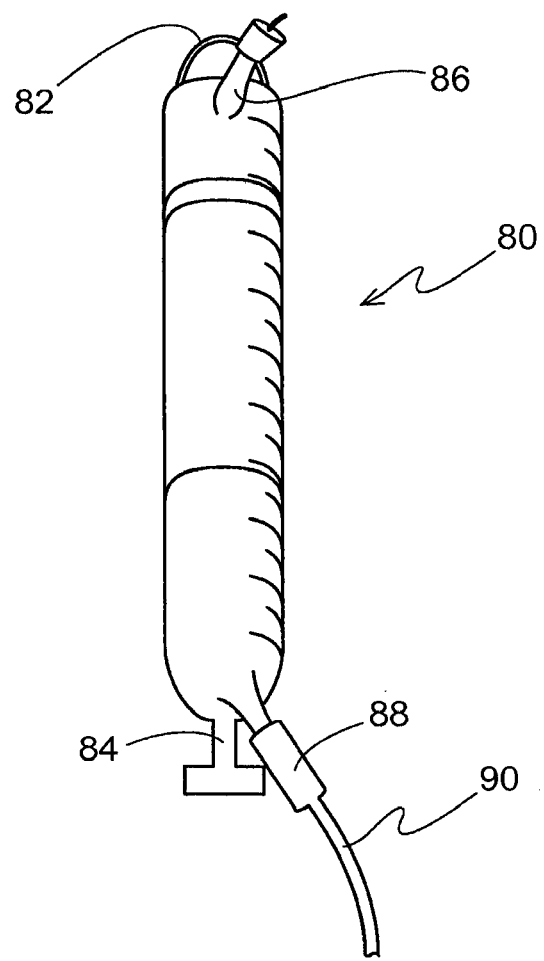
FIG. 7 is a side view of a lipo-grafting bag partially filled with aspirate separated into its components such as by centrifuging.

The tissue aspirated with the cannula, using the syringe driver, is routed by the valves through sterile tubing to cylindrical candle like collapsible bags 80 as shown in FIG. 7 with multiple ports at both ends and a bucket handle type or loop 82 at the top. The bag 80 consecutively functions as: 1—a collection reservoir; 2—a low speed centrifuge tube; 3—a concentration device that allows purging out of the separated serum at the bottom, the free oil and accumulated air at the top through separate vents/ports 84, 86 respectively; 4—a re-injection bag with a port 88 at the bottom connected through tubing 90 to the muting valve in re-injection mode, and graduations that provide reading of the volume of concentrated fat grafted.

Figure 8:
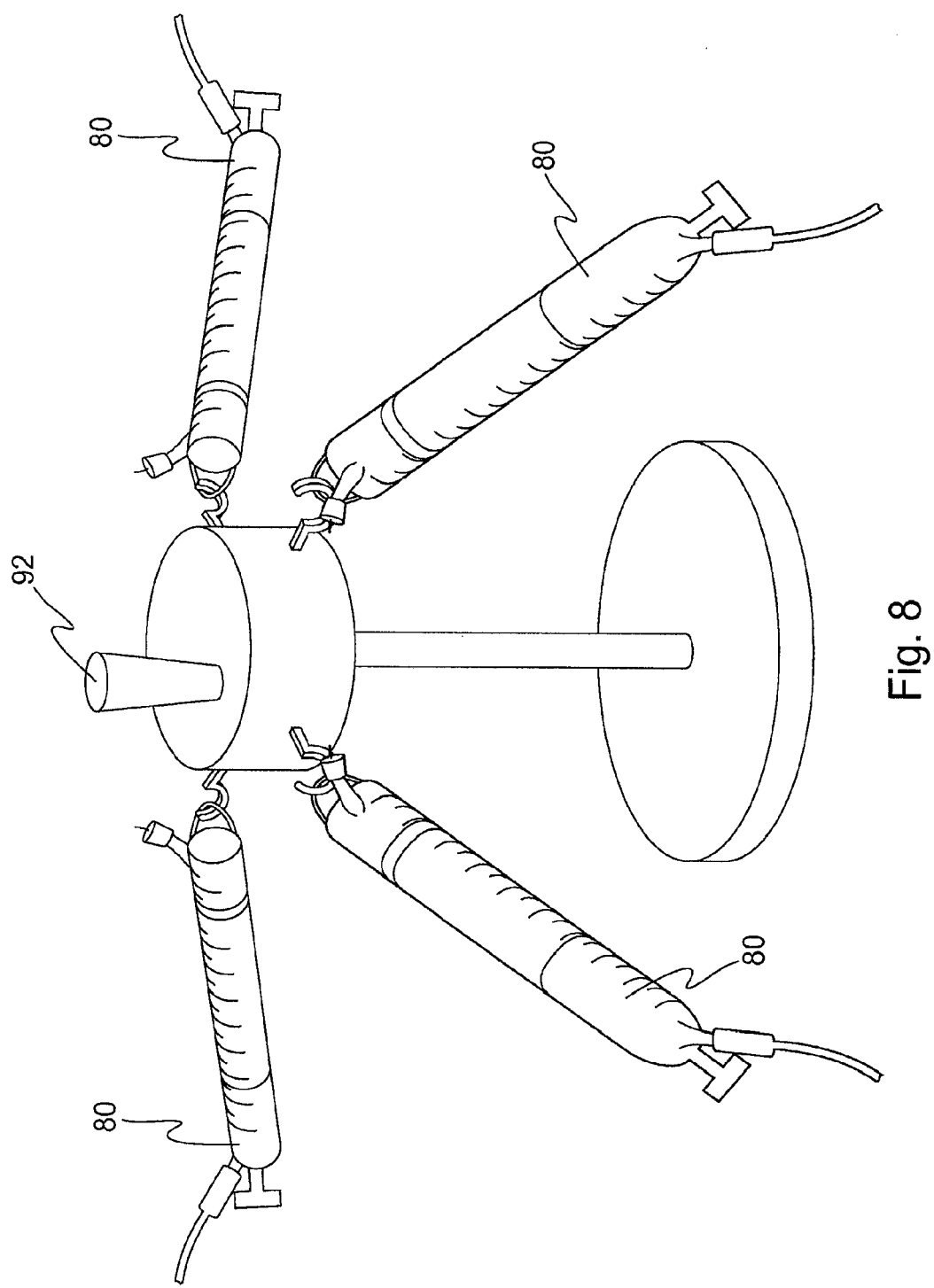
FIG. 8 is a perspective of a manual centrifuge particularly useful in on-the-fly centrifuging during a surgical procedure.

It is generally accepted that high speed centrifugation destroys the fragile adipocytes and while many surgeons still prefer 3000 rpm @ 1-2 minutes centrifugation, there is evidence that even this separation step will lead to loss of valuable components from the aspirated tissue such as stem cells, platelets, and fluid rich in growth factors. Therefore, especially for large volume lipografting many authorities now prefer simple gravity decantation to separate the components of the suctioned fluid. The problem with gravity separation is that it is typically very slow, and especially should the patient be undergoing surgery. To accelerate this process, while avoiding the limitation of a regular centrifuge, the inventors designed a rotating table top hanger 92 as shown in FIG. 8 for the bags 80. The rotation is done manually and the speed is around to 100-200 rpm.

All the above individual inventions are organized to work together in harmony. Together, they comprise a closed harvesting, collection, separation, concentration and re-injection system that inflicts minimal damage to the adipocytes, minimal exposure to air, minimal manipulation of the aspirated material, minimal exchange of syringes and cannulas. In addition, it is practical in that it saves time, effort and supplies, which is especially important to achieve better results with less risk of harm to the patient.

Figure 9:
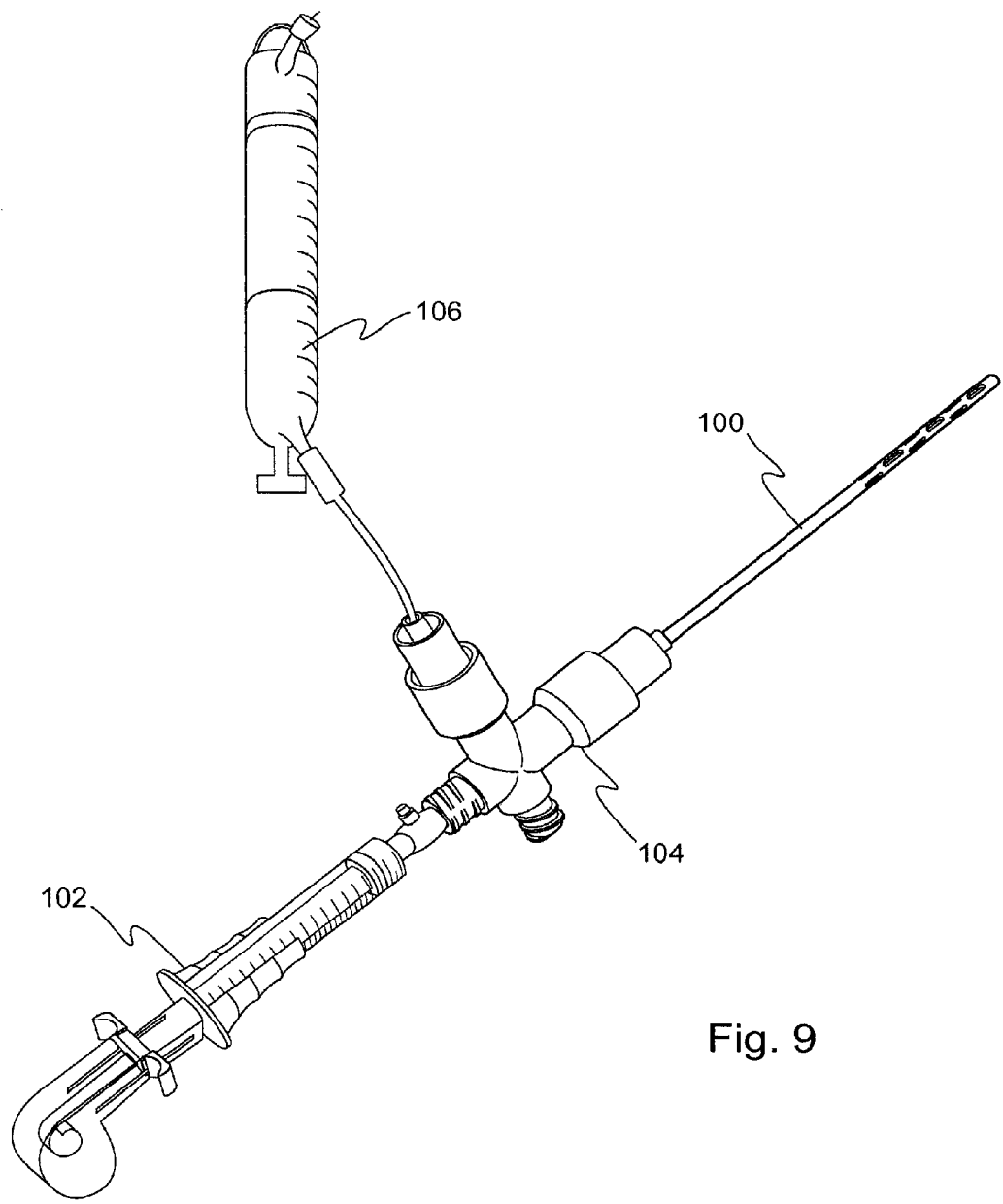
FIG. 9 is a perspective view of the assembled system, having the cannula, routing valve, activated syringe aspirator and lipo-grafting bag all connected in a closed system.

Shown together as a complete closed system in FIG. 9, liposuction is performed with the cannula 100, using the constant pressure device 102, the fat cells are routed by the valves 104 to the collection bag 106 where excess aspirated air is vented. The bags 106 are centrifuged by centrifuge 92 shown in FIG. 8. After centrifugation, the supernatant oil is purged from the upper port and the serum fluid from the bottom port of the bags. The cannula and the constant pressure device are reconnected to the proper ports of the valve, and the bag connected to a different port. The concentrated fat is then re-injected through the tubing connecting the bag to the valve working in injection mode.

The inventors describe a novel device that is especially practical for large volume adipocyte harvesting and grafting. It is believed that this invention reduces operative time and labor while maintaining excellent graft viability and take. By harvesting at a low constant pressure and keeping a closed system with minimal exposure to air, minimal transfer of the aspirate and manipulation of the fat, the inventors have streamlined the harvesting, concentrating and grafting steps and made the procedure practical and reproducible using reduced amounts of supplies, effort, and time.

While the inventors have disclosed their invention in the form of their preferred embodiments, this disclosure should be understood as merely illustrative and not limiting in any sense. Various changes and modifications would be apparent to those of ordinary skill in the art upon reading and learning from the inventors teachings contained herein. Those changes and modifications are fully intended to fall within the scope of the invention which should be limited only by the scope of the claims appended hereto.

What is claimed is:

1. A syringe driver device, comprising:
   a housing for engaging a body of a syringe, wherein the housing extends along an axis that is parallel to the body of the syringe when the syringe is engaged with the housing, and wherein the housing includes an opening in a side of the housing extending along the axis of the housing;
   a bracket for engaging a plunger of the syringe, wherein the bracket extends through the opening in the housing transverse to the axis of the housing; and
   a spring attached to the bracket, the spring being biased to move the bracket and thereby withdraw the plunger from the body of the syringe at a constant force.

2. The syringe device of claim 1 wherein the spring comprises a constant force spring.

3. The syringe device of claim 2 wherein the constant force spring comprises a coiled ribbon spring.

4. The syringe device of claim 2 further comprising a casing for housing the constant force spring.

5. The syringe device of claim 4 wherein the constant force spring comprises a coiled ribbon spring.

6. The syringe device of claim 5 wherein the opening guides movement of the bracket as the bracket moves in an aspirating direction.

7. The syringe device of claim 1 further comprising a casing for housing the spring.

8. A device comprising:
   a syringe having a proximal end and a distal end;
   a plunger slidably received within a body of the syringe and having a first end and a second end, wherein the second end of the plunger extends beyond the distal end of the syringe body;
   a housing engaging an outer surface of the syringe body, wherein the housing includes a first opening and a second opening positioned on substantially opposite sides of the syringe body;
   a bracket engaging the second end of the plunger beyond the distal end of the syringe body, wherein the bracket extends transverse to the syringe body and extends through the first opening and the second opening;
   wherein the bracket is moveable between a first position in which the first end of the plunger is adjacent to a proximal end region of the syringe and a second position in which the first end of the plunger is adjacent to a distal end region of the syringe; and
   a spring connected to the bracket and extending to a distal region of the housing, wherein the spring is configured to move the bracket from the first position to the second position at a constant force.

9. The device of claim 8, wherein the housing is releasably engaged to the outer surface of the syringe body and the bracket is releasably engaged to the plunger.

10. The device of claim 8, wherein the spring includes a coiled ribbon spring.

11. The device of claim 8, wherein moving the bracket from the first position to the second position aspirates the syringe.

12. The device of claim 8, wherein the housing engages a distal end of the syringe body.

13. The device of claim 8, wherein the syringe is removably mounted in the housing.

14. The device of claim 8, wherein the spring applies a substantially constant force to the bracket as the bracket moves the plunger from the first position to the second position to aspirate the syringe.

15. The device of claim 8, wherein movement of the bracket from the first position to the second position defines a stroke length of the bracket and a stroke length of the plunger, and wherein the spring applies a substantially constant force on the bracket along the entire stroke length of the bracket to cause a substantially constant aspirating pressure within the syringe as the plunger moves along the stroke length of the plunger.

16. A device comprising:
a housing located at a proximal region of the device, wherein the housing is dimensioned to receive a distal portion of a syringe, and wherein the housing extends along an axis that runs parallel to the syringe when engaged with the housing, and wherein the housing includes a slot formed in a side of the housing;
a bracket slidably connected to the housing, wherein the bracket extends transverse to the axis of the housing and includes a gripping portion that extends through the slot;
a spring operably coupled to the bracket and extending from the bracket to a distal region of the device; and
a casing located at the distal region of the device, wherein the casing contains at least a portion of the spring,
wherein the bracket is slidable between a proximal region and a distal region of the housing, and the spring is configured to apply a substantially constant force on the bracket to slide the bracket from the proximal region to the distal region of the housing.

17. The device of claim 16, wherein the spring includes a coiled ribbon spring.

18. The device of claim 16, wherein the gripping portion includes a ring.

19. The device of claim 16, wherein the gripping portion includes a curved surface.

20. The device of claim 16, wherein the housing is formed of a first piece and a second piece that are configured to cooperatively engage the syringe.

21. A syringe driver device, comprising:
a syringe;
a housing engaging a body of the syringe, wherein the housing includes a first longitudinal slot extending along the housing and positioned on a first side of the syringe, and wherein the housing includes a second longitudinal slot extending along the housing and positioned on a second side of the syringe, opposite the first side;
a bracket engaging a plunger of the syringe, wherein the bracket extends transversely through the first longitudinal slot and the second longitudinal slot; and
a spring attached to the bracket, the spring being biased to move the bracket and thereby withdraw the plunger from the body of the syringe at a constant force.

22. A device comprising:
a syringe having a proximal end and a distal end;
a plunger slidably received within a body of the syringe and having a first end and a second end, wherein the second end of the plunger extends beyond the distal end of the syringe body;
a housing engaging an outer surface of the syringe body, wherein the housing includes a longitudinal slot extending along an axis of the housing substantially parallel to an axis of the syringe, wherein the slot forms an opening through a side of the housing;
a bracket that extends along an axis transverse to the axis of the housing and the axis of the syringe, wherein the bracket engages the second end of the plunger beyond the distal end of the syringe body, wherein the bracket extends transversely through the longitudinal slot;
wherein the bracket is moveable between a first position in which the first end of the plunger is adjacent to a proximal end region of the syringe and a second position in which the first end of the plunger is adjacent to a distal end region of the syringe; and
a spring connected to the bracket and extending to a distal region of the housing, wherein the spring is configured to move the bracket from the first position to the second position at a constant force.

23. A device comprising:
a syringe;
a housing located at a proximal region of the device, wherein the housing receives a distal portion of the syringe and extends substantially parallel to a longitudinal axis of the syringe;
a first longitudinal slot extending along a first side of the housing;
a second longitudinal slot extending along a second side of the housing such that the syringe is positioned between the first longitudinal slot and the second longitudinal slot;
a bracket engaging a plunger of the syringe and slidably connected to the housing along an axis transverse to the longitudinal axis of the syringe, wherein the bracket includes a gripping portion that extends transversely through the first longitudinal slot and the second longitudinal slot and projects out from the first longitudinal slot and the second longitudinal slot;
a spring operably coupled to the bracket and extending from the bracket to a distal region of the device; and
a casing located at the distal region of the device, wherein the casing contains at least a portion of the spring,
wherein the bracket is slidable within the first longitudinal slot and the second longitudinal slot between a proximal region and a distal region of the housing, and the spring is configured to apply a substantially constant force on the bracket to slide the bracket from the proximal region to the distal region of the housing.

\* \* \* \* \*